United States Patent
Dakin et al.

(10) Patent No.: US 6,903,234 B2
(45) Date of Patent: Jun. 7, 2005

(54) METHOD OF MAKING A CALCIUM SALT OF 2-HYDROXY-4-(MERCAPTOMETHYL) BUTANOIC ACID

(75) Inventors: Roger G. Dakin, Swindon (GB); Sarel W. Du Toit, Stellenbosch (ZA); Richard A. Houseman, North Yorkshire (GB); David G. Stedman, Benoni (ZA)

(73) Assignee: Technical and Commercial Services International Limited, Yorkshire (GB)

(*) Notice: Subject to any disclaimer, the term of this patent is extended or adjusted under 35 U.S.C. 154(b) by 25 days.

(21) Appl. No.: 10/416,282

(22) PCT Filed: Nov. 7, 2001

(86) PCT No.: PCT/IB01/02087

§ 371 (c)(1),
(2), (4) Date: Sep. 19, 2003

(87) PCT Pub. No.: WO02/38539

PCT Pub. Date: May 16, 2002

(65) Prior Publication Data

US 2004/0054225 A1 Mar. 18, 2004

(30) Foreign Application Priority Data

Nov. 9, 2000 (ZA) .......................................... 2000/6482
Mar. 28, 2001 (ZA) .......................................... 2001/2553

(51) Int. Cl.$^7$ ............................................. C07C 323/22
(52) U.S. Cl. ....................................... 562/581; 562/580
(58) Field of Search ................................. 562/581, 580

(56) References Cited

U.S. PATENT DOCUMENTS 4,335,257 A 6/1982 Cummins et al. ........... 562/581

FOREIGN PATENT DOCUMENTS

EP 0140865 A1 5/1985

*Primary Examiner*—Bernard Dentz
(74) *Attorney, Agent, or Firm*—Sheridan Ross PC

(57) ABSTRACT

A method of making calcium-2-hydroxy-4-(mercaptomethyl)butanoate includes combining and mixing 2-hydroxy-4-(mercaptomethyl)butanoic acid and a calcium salt selected from calcium oxide and calcium hydroxide and water in a first reaction zone. The combining and mixing step is carried out over a first period of 3–120 seconds. The resulting reaction mixture is transferred at the end of the first period from the first reaction zone to a second reaction zone, the transferring step being carried out over a second period of 3–60 seconds. Heat generated by reaction between the 2-hydroxy-4-(mercaptomethyl)butanoic acid and the calcium salt in the second reaction zone is allowed to drive off sufficient water to produce a product mixture containing less than 5% (m/m) water.

25 Claims, 3 Drawing Sheets

METHOD OF MAKING A CALCIUM SALT OF 2-HYDROXY-4-(MERCAPTOMETHYL) BUTANOIC ACID

This application is a 371 of PCT/IB01/02087 filed Nov. 7, 2001.

THIS INVENTION relates to the calcium salt of 2-hydroxy-4-(mercaptomethyl)butanoic acid.

It relates in particular to a method of making the calcium salt of 2-hydroxy-4-(mercaptomethyl)butanoic acid and to the calcium salt of 2-hydroxy-4-(mercaptomethyl)butanoic acid made in accordance with the method. For brevity, the calcium salt of 2-hydroxy-4-(mercaptomethyl)butanoic acid, which has the formula $[CH_3S(CH_2)_2CH(OH)COO]_2Ca$, is referred to hereinafter as calcium-2-hydroxy-4-(mercaptomethyl) butanoate.

According to a first aspect of the invention, there is provided a method of making calcium-2-hydroxy-4-(mercaptomethyl)butanoate, the method including the steps of combining and mixing 2-hydroxy-4-(mercaptomethyl) butanoic acid and a calcium salt selected from calcium oxide and calcium hydroxide and water in a first reaction zone, the combining and mixing step being carried out over a first period of 3–120 seconds to produce a reaction mixture in the first reaction zone;

transferring the resulting reaction mixture at the end of the first period from the first reaction zone to a second reaction zone, the transferring step being carried out over a second period of 3–60 seconds; and allowing heat generated by reaction between the 2-hydroxy-4-(mercaptomethyl)butanoic acid and the calcium salt in the second reaction zone to drive off sufficient water to produce a product mixture containing less than about 5% (m/m) water.

The percentage (m/m) refers to a mass per mass percentage.

The first period may be 5–20 seconds. The second period may be 5–45 seconds.

The 2-hydroxy-4-(mercaptomethyl)butanoic acid may be in the form of an aqueous solution. The aqueous solution may have a concentration of 65–95% by mass of the 2-hydroxy-4-(mercaptomethyl)butanoic acid. Preferably it will have a concentration of 70–90% by mass. Typically, an approximately 89% aqueous solution of 2-hydroxy-4-(mercaptomethyl)butanoic acid is used. The compound is referred to as methionine hydroxy analogue free acid and is commercially available. The method may include the prior step of mixing the acid and water. The acid and the water may thus be kept in separate storage tanks.

The mass ratio between the aqueous acid solution and the calcium salt will typically be between about 70–90% of the aqueous solution (expressed as an 88% aqueous solution), about 10–30% of the calcium salt and about 0–20% water (as added water) and will be affected by the purity of the acid and the salt.

Thus the combining and mixing steps may be conducted so that the reaction mixture contains 70–90% by mass of the aqueous solution, 10–30% by mass of the calcium salt and 0–20% by mass water.

Preferably, the method will include allowing the heat generated to drive off sufficient water to produce a product mixture containing less than about 4,5% water and more preferably less than about 2%.

The combining step may include adding the calcium salt to the solution of 2-hydroxy-4-(mercaptomethyl)butanoic acid. The method may include the prior step of warming the solution of 2-hydroxy-4-(mercaptomethyl)butanoic acid to about 50–130° C. and preferably to about 70–85° C.

The duration of the combining and mixing step will vary with the amounts of the acid and calcium salt and with the nature of the calcium salt. For example, in the case of calcium oxide, the time to combine the acid and the calcium salt will vary from a lower level of about 3–10 seconds for an amount of about 55–65 kg of the acid and preferably about 60 kg of the acid and about 9–18 kg of the calcium oxide/hydroxide to an upper level of about 3–30 seconds for an amount of about 500 kg of the acid and about 75–150 kg of the calcium oxide/hydroxide. As the discharge of any water required can be done simultaneously with the acid, no extension of the charging time will be brought about by water addition.

The duration of the second period will vary similarly. In the case of calcium oxide the duration of the second period will vary from a lower level of about 3–15 seconds for an amount of about 55–65 kg of the acid and preferably about 60 kg of the acid and about 9–18 kg of the calcium oxide/hydroxide to an upper level of about 3–20 seconds for an amount of about 450–550 kg of the acid and preferably about 500 kg of the acid and about 75–150 kg of the calcium oxide/hydroxide. The addition of water will generally shorten the second period.

Thus the salt may be calcium oxide and 55–65 kg of the aqueous solution may be combined with 9–18 kg of the calcium salt over a first period of about 3–10 seconds. The duration of the second period may then be about 3–15 seconds.

Instead, the salt may be calcium oxide and about 450–550 kg of the aqueous solution may be combined with about 75–150 kg of the calcium salt over a first period of 3–30 seconds. The duration of the second period may then be about 3–20 seconds.

The method may include the further steps of successively combining and mixing a plurality of batches of the acid, calcium salt and water in the first reaction zone to produce successive batches of the reaction mixture and successively transferring each of the batches to the same second reaction zone.

The second reaction zone may be a receiving vessel and several batches of reaction mixture may be transferred into the same receiving vessel until the receiving vessel is full or contains a predetermined quantity of the reaction mixture. The receiving vessel may then be replaced with a second receiving vessel and further batches may be added to the second receiving vessel. This process may be continued until the initially used receiving vessels have been emptied so that they can be reused. It is an advantage of this embodiment of the invention that the reaction vessel and all of the receiving vessels can be kept within an enclosed area so that steam and fumes produced in the reaction between the acid and the calcium salt can be extracted and dealt with by an appropriate disposal system.

In an example of this embodiment of the invention, a material dosing system, controlled by a programmable logic controller or similar suitable control unit, weighs out the raw materials in sequence into a mixing vessel. The agitator in the mixing vessel starts immediately on receiving a signal that the first of the pre-heated acid has been dosed. Optionally there can be an operator-controlled delay between the opening of the acid dosing valves and the beginning of the agitation.

Thus the method may be one in which a material dosing system controlled by a programmable logic controller, weighs out the raw materials into the first reaction zone.

Once agitation has begun, the calcium salt is dosed. The raw materials are then mixed for a specific time before being discharged into a receiving vessel. Additional batches are then dosed into the same reaction vessel and discharged into the receiving vessel until the amount of material in the receiving vessel has reached a desired level. Optionally, the material in the receiving vessel can also be agitated. Once the desired level in the receiving vessel has been reached, it is removed from the dosing area and replaced by a fresh receiving vessel. The process then continues with reaction mixtures being charged into the fresh receiving vessel. The first receiving vessel can then be moved to another location whilst the reaction proceeds to completion with the heat produced driving off water. There is essentially no limit to the number of receiving vessels that can be employed and the size of the reaction vessels can be selected to suit the residence time required to ensure complete reaction and a desired output.

In another example of this embodiment of the invention, using calcium oxide as the calcium salt, the required amount of a pre-warmed solution of 2-hydroxy-4-(mercaptomethyl) butanoic acid is added to a mixing vessel fitted with an agitator and the required amount of pre-weighed calcium oxide is rapidly added to the solution under vigorous agitation. The addition typically takes about 3–10 seconds depending upon the volume of the solutions and the mass of the calcium oxide. Reaction between the acid in the solution and the calcium oxide usually starts within 5–30 seconds, depending upon the reactivity of the calcium oxide, the temperature of the acid solution and the concentration of the acid, and is accompanied by a rapid temperature rise to about 120° C. within 5–30 seconds for small batches. The temperature rise in larger batches is usually less rapid, taking up to 10 minutes to rise to 120° C. The mixture is immediately discharged into a receiving vessel or onto a flat surface. These process steps are repeated several times and the several resulting batches are discharged on top of one another. The number of batches is determined by the size of the mixing vessel and the rate of loss of water from the reacting magma. When the receiving vessel is full, further batches are discharged into a fresh receiving vessel. Once the material in the first receiving vessel is dry enough (i.e. typically having a water content of less than about 10% and usually less than about 5%), the contents are discharged and the vessel is reused. The contents of the first receiving vessel are generally discharged when the second receiving vessel is full and the contents of the second vessel are discharged when the first vessel is full. The discharged material is allowed to cool with occasional agitation to allow heat to escape. The final product is then dressed according to size and packaged.

Preferably, the reaction vessels will be designed to have no sharp internal corners or edges. The vessels will also preferably be lined with an inert material such as a layer of PTFE (polytetrafluoroethylene) or a similar material. The top of the mixing/reaction vessel will preferably be provided with an extraction system for extracting of steam and vapours. The inner lining material serves to reduce adhesion between the reactants, the product and the vessel to facilitate rapid discharge when the vessel is tipped.

According to a second aspect of the invention, there is provided a method of making calcium-2-hydroxy-4-(mercaptomethyl)butanoate, the method including the steps of combining and mixing 2-hydroxy-4-(mercaptomethyl) butanoic acid, a calcium salt selected from calcium oxide and calcium hydroxide and water in a first reaction zone to produce a reaction mixture in the first reaction zone; and continuously transferring the reaction mixture from the first reaction zone to a second reaction zone, the reactants being added to the first reaction zone in successive batches and the reaction mixture being continuously removed from the first reaction zone at a rate which is selected so that the residence time of the reaction mixture in the first reaction zone is between about 3 and 120 seconds; and allowing heat generated by reaction between the 2-hydroxy-4-(mercaptomethyl)butanoic acid and the calcium salt in the second reaction zone to drive off sufficient water to produce a product mixture containing less than about 10% water.

Preferably the method will involve allowing heat generated to drive off sufficient water to produce a product mixture containing less than about 5% water.

The rate of removal of the reaction mixture from the first reaction zone will depend on the production capacity of the installation and may vary between about 500 and about 30000 kg per hour.

According to another aspect of the invention, there is provided a continuous method of making calcium-2-hydroxy-4-(mercaptomethyl)butanoate, the method including the steps of simultaneously feeding, into a reaction zone, an aqueous solution of 2-hydroxy-4-(mercaptomethyl)butanoic acid, at a rate of approximately 500–30000 parts per hour, and a calcium salt selected from calcium oxide and calcium hydroxide, at a rate of approximately 75–6200 parts per hour, to produce a reaction mixture in the reaction zone; and transferring the reaction mixture from the reaction zone to a second zone at a rate which is selected so that the residence time of the reaction mixture in the reaction zone is sufficient to allow heat generated by reaction between the 2-hydroxy-4-(mercaptomethyl)butanoic acid and the calcium salt in the reaction zone to drive off sufficient water to produce a product mixture containing less than about 5% water.

The rate will preferably be selected so that the residence time of the reaction mixture in the reaction zone is 5–30 minutes.

In an example of this embodiment of the invention, a pre-warmed solution of 2-hydroxy-4-(mercaptomethyl) butanoic acid, at a temperature of about 50–130° C. and preferably at a temperature of about 70–85° C., is transferred at a controlled rate into a mixing chamber. The incorporation of water would change these temperatures. Calcium oxide is simultaneously added to the mixing chamber at a controlled rate. At the start of the continuous process the outlet from the mixing chamber is kept closed. This allows reacting material to build up in the mixing chamber and the temperature to rise so that the chamber is effectively both a mixing and a reaction zone. The temperature of the material in the chamber rapidly rises to about 100–170° C. with the evolution of water as steam. Once the initial reaction is over and a powdery product has formed, addition of the warm solution and the calcium oxide is resumed. The rate of addition of the solution and the calcium oxide is selected so that the residence time in the vessel is sufficient to allow the 2-hydroxy-4-(mercaptomethyl)butanoic acid and the calcium oxide to react and for water to be driven off. The residence time is typically about 5–30 minutes. Addition of the solution and the calcium oxide then continues and the outlet from the mixing chamber is opened so that the reaction product is discharged. The amount of product remaining in the chamber is controlled at all times to ensure that a suitably dry product is continuously discharged from the chamber at a controlled rate. The reaction product is discharged onto a surface or into a den and left to cool or taken for further processing as required.

According to another aspect of the invention, there is provided a continuous method of making calcium-2-hydroxy-4-(mercaptomethyl)butanoate, the method including the steps of simultaneously feeding, into a reaction zone, an aqueous solution of 2-hydroxy-4-(mercaptomethyl)butanoic acid, at a rate of approximately 500–30000 parts per hour, and a calcium salt selected from calcium oxide and calcium hydroxide, at a rate of approximately 75–6200 parts per hour, to produce a reaction mixture in the reaction zone; and transferring the reaction mixture from the reaction zone to a second zone at a rate which is selected so that the residence time of the reaction mixture in the reaction zone is sufficient to initiate reaction between the 2-hydroxy-4-(mercaptomethyl)butanoic acid and the calcium salt but not sufficient to drive off water from the reaction mixture and allowing heat generated by further reaction between the 2-hydroxy-4-(mercaptomethyl)butanoic acid and the calcium salt in the second zone to drive off sufficient water to produce a product mixture containing less than about 5% water.

The rate of addition of the acid and the salt will depend upon the production capacity of the plant in which the process is conducted. Production levels of 1–30 tons per hour can be achieved by the method of the invention.

In an example of this embodiment of the invention, the amount of material retained in the mixing chamber is less and the mixing chamber serves only to mix the two reactants and to allow reaction to initiate. In this case the residence time in the mixing zone is about 5–60 seconds. Further reaction and water loss from the reaction mixture then continues after the mixture has been discharged from the mixing vessel. The product is then screened or packaged as described above.

The reaction mixture in the mixing/reaction zone may be transferred on an endless moving belt so that the second zone is formed by the belt. The reactants will then react whilst being carried on the belt. The length of the belt and the speed of the belt will be selected so that, when the material is discharged from the belt, the resulting product mixture contains the desired amount of water. The belt will preferably be enclosed so that steam and fumes produced by reaction between the acid and the calcium salt can be extracted and dealt with by an appropriate disposal system as described above.

Preferably, at the point of discharge from the belt, the material will be passed through a rotating cutter, to reduce the particle size and to release trapped steam and gases in the product. The product will then be transported on a conveyor or suitable handling device for further processing as required, for example for granulation, drying, cooling, dressing or bagging.

There are several important advantages associated with this embodiment of the invention. Because there is minimal mixing of the product after the initial feeding and mixing stage, energy requirements of the process are reduced. Furthermore, when the product passes through the plastic stage, no mechanical agitation takes place. There is therefore no contact between a mixing device and the thickening product and no build-up or aggregation of material in the mixing vessel or on the agitator. It has been found that this largely removes the requirement of high pressure steam cleaning of equipment and the resulting effluent problem. It is also an advantage that the entire reaction system is enclosed. This allows relatively easy removal of steam, water vapour and gases produced in the reaction. The Applicant has also found that there is no need for recycle or heel material. This effectively increases the production throughput for equipment of a given size. Prior art methods known to the Applicant require the addition of recycle or heel material.

In an example of this embodiment of the invention, the hot aqueous acid solution is weighed out into the mixing/reaction vessel. The agitator is started and the calcium oxide or calcium hydroxide is dosed. After a predetermined period, the outlet valve of the mixing vessel opens and the contents discharge onto an endless enclosed belt running, typically, between two pulleys.

In this embodiment of the invention an agitator can be included at the beginning of the belt close to the discharge from the mixing/reaction vessel to ensure that complete mixing takes place before the material passes from the fluid stage. Preferably, the initial part of the belt has a U-shaped cross-section in order to hold the relatively fluid reaction mixture. The initial part of the belt is also arranged to slope downwardly from the reaction vessel to prevent reverse flow or spillage of material. The U-shaped section is selected to have a volume which is sufficient to hold up to 30 minutes' of plant production capacity. During this period, the reaction mixture passes through a fluid and then a plastic stage with the evolution of steam and gases. At the end of the U-shaped section, the belt flattens out to almost its full width but remains slightly curled at the outside edges to minimize the risk of spillage. At the point at which the belt flattens out, the product has already partially dried. The flattening of the belt causes the cake to split open to release steam, moisture and gases trapped inside the cake. The thickness of the cake on the belt generally varies between about 10 and about 90 cm. The cake is then carried by the belt, drying as it moves and, at the end of the belt, the cake falls into a crumbling device. This reduces the particle size of the product and releases steam, moisture and trapped gases. The product is then transported to a second locality for treatment such as granulation, drying, cooling, enrichment, sizing or bagging.

In a preferred embodiment, the entire belt is enclosed by a canopy. Air is drawn through the enclosed space carrying with it steam, water vapour, fumes and gases produced in the reaction. The extracted gases are treated in a suitable treatment plant.

Preferably the belt will be made of a suitable high temperature resistant material, PTFE, thin stainless steel, wooden slats or the like. The release-nature of the belt is also important. The belt must be sufficiently smooth to allow the product to drop off the belt as it passes around the final pulley. Ideally, no material should adhere to the belt. The enclosed belt system will typically have a width of about 2 m a length of approximately 25 m and a maximum height of about 2 m.

In other embodiments of the invention, the calcium salt is replaced with a metal salt selected from magnesium oxide, sodium hydroxide and potassium hydroxide.

Thus, according to another aspect of the invention there is provided a method of making a salt of 2-hydroxy-4-(mercaptomethyl)butanoate, the salt being a salt of a metal selected from magnesium, sodium and potassium and the method including the steps of combining and mixing 2-hydroxy-4-(mercaptomethyl) butanoic acid and a base selected from magnesium oxide, sodium hydroxide and potassium hydroxide in water in a first reaction zone, the combining and mixing step being carried out over a first period of 3–120 seconds to produce a reaction mixture in the first reaction zone;

transferring the resulting reaction mixture at the end of the first period from the first reaction zone to a second reaction zone, the transferring step being carried out over a second period of 3–60 seconds; and allowing heat generated by reaction between the 2-hydroxy-4-(mercaptomethyl)butanoic acid and the base in the second reaction zone to drive off sufficient water to produce a product mixture containing less than 5% (m/m) water.

The invention extends to a magnesium, sodium or potassium salt of 2-hydroxy-4-(mercaptomethyl)butanoate prepared by a method as hereinbefore described.

Where the raw materials, or reactants, are dosed on a batch basis, the dosage can be by weight or volume. Where the reactants are dosed on a continuous basis, the amount dosed will be measured by a belt weigher, mass flow meter or a similar dosing device.

The invention is now described, by way of example, with reference to the following Examples and the drawings in which FIG. 1 shows a schematic plan view of an installation for use in the method of the invention;

EXAMPLE 1

Batch Process

Figure 1:
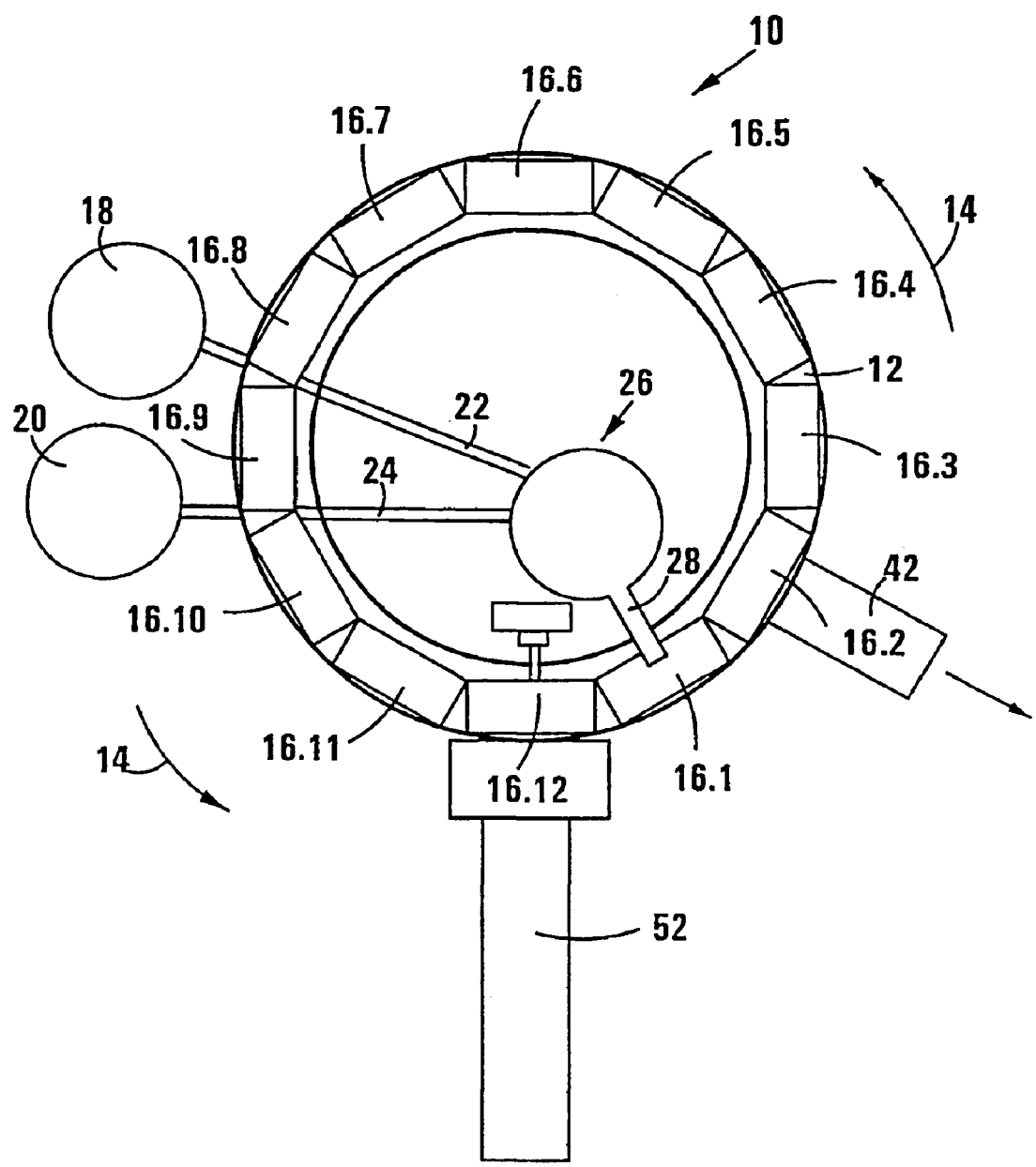

2-Hydroxy-4-(mercaptomethyl)butanoic acid (89% aqueous solution; 1008 g; specific gravity 1.24) was heated to 84° C. in a 2.5 l vessel and calcium oxide (177 g) was rapidly added to the heated liquid. The calcium oxide contained 93% as CaO and 0.5% as MgO. The addition took less than about 5 seconds. The resulting mixture was thoroughly stirred for 15 seconds and then poured into a receiving vessel and left to stand without any further stirring. The mixing, stirring and pouring steps took less than about 30 seconds. The temperature of the mixture rose rapidly to about 90° C. in about 60 seconds and then continued to rise over a period of about 25 minutes to a maximum of about 139° C. The mass of the mixture was monitored for 40 minutes after it had been poured into the receiving vessel to measure water loss due to evaporation from the hot mixture.

The time, temperature and mass are set out below:

| TIME(min) | TEMPERATURE(° C.) | MASS(g) |
|---|---|---|
| 15 | 134 | 1106 |
| 20 | 137 | 1101 |
| 25 | 139 | 1096 |
| 30 | 136 | 1094 |
| 40 | 126 | 1093 |

The reaction mixture was then turned over several times to allow additional moisture to escape. The final mass was 1050 g. The mixture was screened into two fractions which were designated as "coarse" (particle size 4.00–0.5 mm; 653 g) and "fine" (particle size less than 0.5 mm; 380 g). Approximately 17 g of material was lost during the screening process. Each fraction was analysed for monomer acid content. The "coarse" fraction contained 86.5% and the "fine" fraction 83.9% of the monomer acid. The above values correspond to 97.4% for the "coarse" and 94.5% for the "fine" expressed as calcium-2-hydroxy-4-(mercaptomethyl)butanoate.

EXAMPLE 2

Batch Process

2-Hydroxy-4-(mercaptomethyl)butanoic acid (89% aqueous solution; 10.00 kg) was heated to 73° C. and calcium oxide (1,768 kg) was rapidly added to the heated liquid with agitation. The calcium oxide contained 93% as CaO and 0.5% as MgO. The addition took about 8 seconds. The resulting mixture was thoroughly stirred for about 3 minutes, using an electric drill fitted with a blade resembling a kitchen whisk, during which time the temperature initially dropped to 63° C. and then rose to 90° C. The mixture was then poured into a receiving vessel and left to stand without any further stirring. The mixing, stirring and pouring steps took about 4 minutes. The temperature of the mixture rose rapidly to boiling point (about 121° C.) in about 7 minutes. A second batch of 2-hydroxy-4-(mercaptomethyl)butanoic acid (89% aqueous solution; 10.00 kg) and calcium oxide (1.768 kg) was mixed in the same way and added to the same receiving vessel and the combined mixture was left for 90 minutes and weighed. The water loss after 90 minutes was found to be 2246 g. The weight was 21290 g. The product was then poured out onto a flat tray. After 16 hours the product was re-weighed and the water loss was found to be 2861 g. It was then screened, sampled and analysed. The monomer acid content of the product was 85.1% corresponding to 95.8% expressed as calcium-2-hydroxy-4-(mercaptomethyl) butanoate.

EXAMPLE 3

Batch Process

Successive batches of 2-hydroxy-4-(mercaptomethyl) butanoic acid (89% aqueous solution; specific gravity 1.24) and calcium oxide (unslaked lime, CaO content 93%, MgO content 0.5%) were mixed and, in each case, agitated until the temperature reached about 80–90° C. The batches were then successively dropped into a 50 l capacity container. The maximum temperature reached in the container was approximately 219° C. After 40 minutes, the resulting product was dry and free-flowing. The bed depth in the container was 15 cm. After 16 hours even the sticky moist product which had adhered to the top and edges of the container had dried.

Details of the batches are set out below.

| BATCH NO. | LIQUID HMBA (g) | CaO (g) | TEMPERATURE (° C.) |
|---|---|---|---|
| 1 | 1004 | 177 | 74 |
| 2 | 1008 | 177 | 70 |
| 3 | 1003 | 177 | 72 |
| 4 | 1004 | 180 | 69 |
| 5 | 1005 | 178 | 63 |
| 6 | 1002 | 178 | 70 |
| TOTAL | 6026 | 1067 | |

The product analysed at 85.6% monomer acid content, 13.1% Ca and 2.3% free moisture.

EXAMPLE 4

Batch Process

2-Hydroxy-4-(mercaptomethyl)butanoic acid (89% aqueous solution; 100 g) was heated to 77° C. and calcium oxide (18.8 g) was rapidly added to the heated solution with agitation. The calcium oxide contained 90% as CaO and 2.3% as MgO. The mixture was intensively mixed by hand in a large container and the temperature rapidly rose to 123° C. The product went through a plastic stage and then broke up into a free-flowing powder. The yield was 104.5 g of the calcium salt with an analysis of 85.29% monomer acid content and 2.1% free moisture.

EXAMPLE 5

Totally Enclosed Batch Process

Referring to the drawings, reference numeral 10 generally indicates an installation for the continuous production of calcium 2-hydroxy-4-(mercaptomethyl)butanoate. The installation 10 includes a carousel 12 which rotates in the direction of the arrows 14. Twelve hoppers 16.1–16.12 are mounted on the carousel 12.

The installation 10 includes a calcium oxide silo 18 and a storage tank 20 which holds a preheated 88% aqueous solution of 2-hydroxy-4-(mercaptomethyl)butanoic acid. Feed lines 22, 24 extend from the silo 18 and the tank 20 to a mixing installation 26 which includes a mixing vessel (not shown) and a measuring device (not shown) for measuring the volume or mass of the calcium oxide and the aqueous acid. A feed line 28 extends from the mixing installation 26 for feeding the reaction mixture into the hoppers 16.1–16.12.

Figure 2:
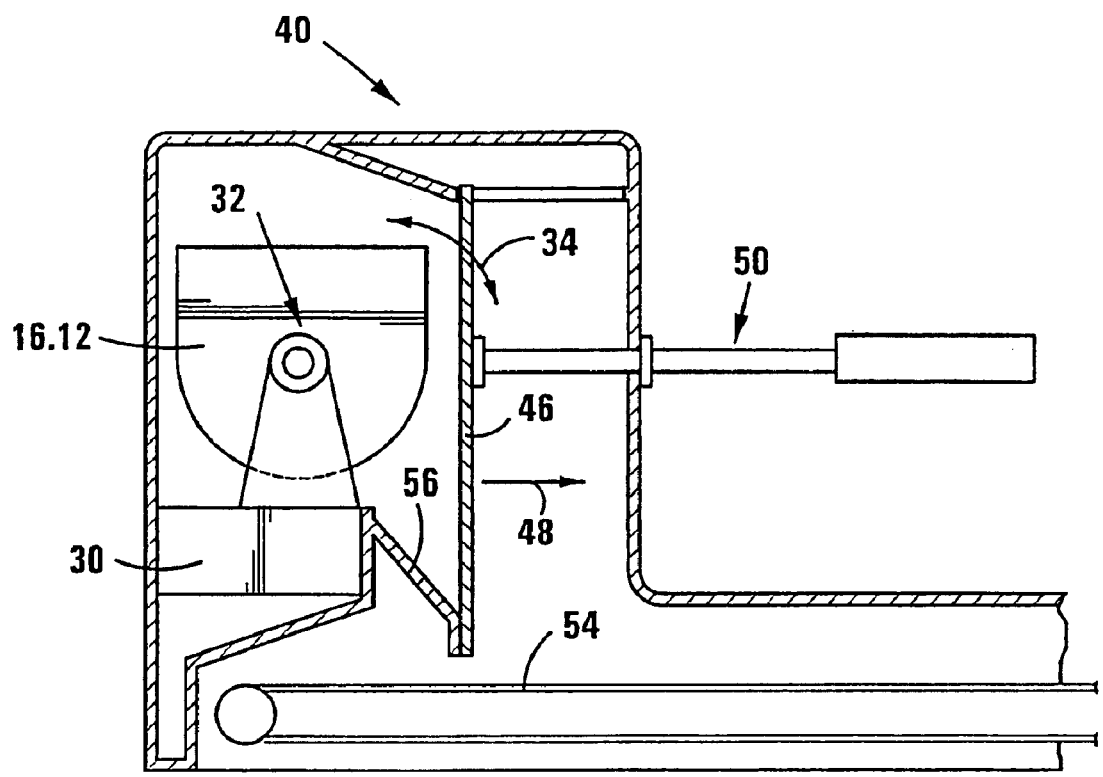
FIG. 2 shows a schematic side view of part of the installation of FIG. 1 with a hopper in an upright position.
Figure 3:
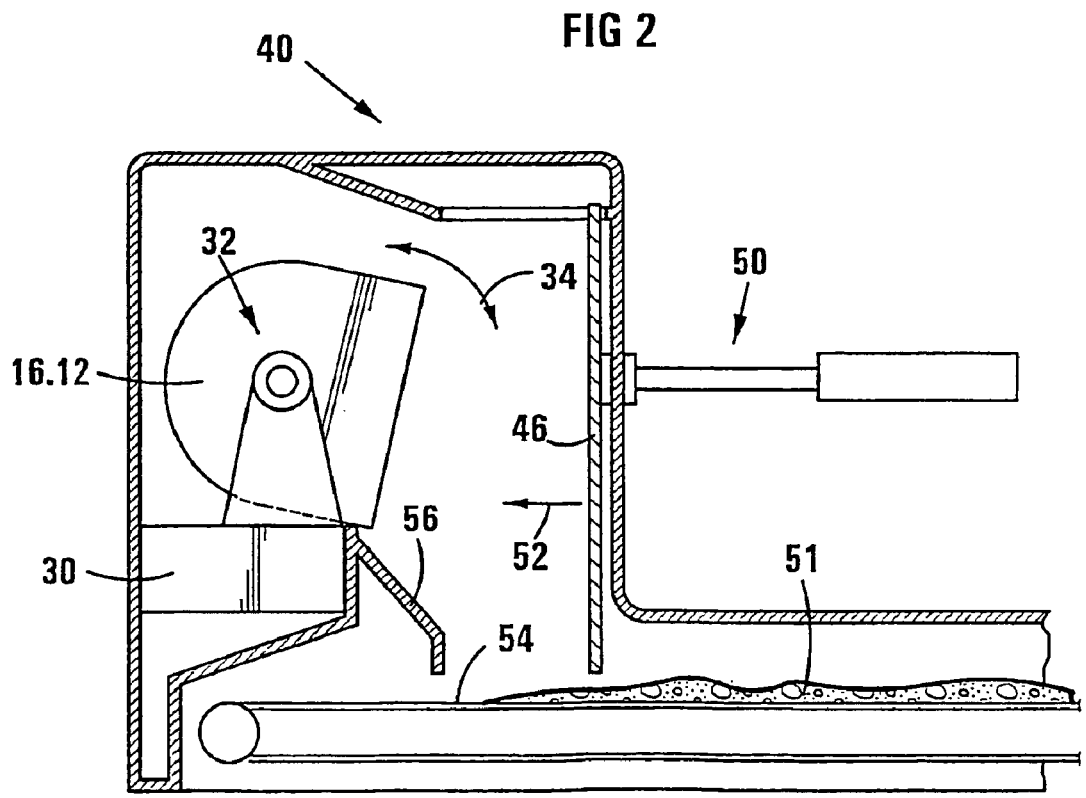
FIG. 3 shows the side view of FIG. 2 with the hopper in a tilted position.

FIGS. 2 and 3 show the hopper 16.12 and a part of the carousel 12 in further detail. The carousel 12 includes a rotatable support platform 30 on which the hoppers 16.1–16.12 are mounted on pivot mechanisms generally indicated by reference numeral 32 so that each hopper can be tilted in the direction of the arrow 34 as shown in FIG. 3. A hydraulic arm, (not shown) operates to tip the hoppers so that the reaction mixture can be discharged. The installation 10 further includes a spillage plate 56.

The carousel 12 and the hoppers 16.1–16.12 are enclosed in an annular tunnel structure 40 (FIGS. 2 and 3) which is provided with an extractor 42 (FIG. 1). The tunnel structure 40 is provided with a door 46 which opens in the direction of the arrow 48 by a hydraulic ram mechanisms 50 when a hopper 16.1–16.12 is tipped as shown in FIG. 3. When the hopper 16.1–16.12 returns to its upright position on the carousel 12, the door 46 closes again in the direction of the arrow 52. Material 51 tipped from the hopper is optionally passed through the crumbler (not shown) and falls onto a conveyor belt 54 from where it is conveyed to a receiving vessel.

In this embodiment of the invention, calcium oxide and the acid are mixed in batches to produce 62.5 kg of product in the mixing vessel for up to 45 seconds for each batch and the reaction mixture is then transferred into one of the hoppers 16.1–16.12 over a period of approximately 3–10 seconds. About 16 batches are added to each of the hoppers 16.1–16.12 so that each hopper holds approximately 1 metric ton of the reaction mixture. Each hopper 16.1–16.12 is accordingly filled in about 12 minutes. When a hopper is full, the carousel 12 rotates so that the next hopper is positioned below the feed line 28 to be filled. Ten of the hoppers are filled over a period of 2 hours. When the first hopper reaches a position opposite the conveyor belt 54, corresponding to hopper 16.12 the hydraulic arm tips the hopper so that the reaction mixture, which has by then been reacting for up to 2 hours, is tipped (optionally via the crumbler) onto the conveyer belt 54. In this embodiment of the invention, the installation will produce approximately 5 tons of product per hour.

In another embodiment of this version of the invention, the hoppers 16.1–16.12 are larger and the aqueous acid and the calcium oxide are combined in batches, as described above, at a rate of approximately 5.8 tons per hour of the aqueous acid and 1.13 tons per hour of the calcium oxide to produce about 6 tons per hour of product. The actual amounts of the aqueous solution, the water and the calcium salt dosed and the time that the reactants remain in the hoppers will depend upon the desired throughput and the purity of the raw materials. The rates of addition and the quantities will be adjusted accordingly.

In other embodiments of this version of the invention, the sizes of the hoppers 16.1–16.12 are varied and the rate of addition of the calcium oxide is accordingly varied between about 315 and about 6200 kg per hour and the rate of addition of the aqueous acid is varied between about 1 500 and about 30 000 kg per hour. The method of the invention can thus produce as much as 30 tons per hour, or more, of the calcium salt.

EXAMPLE 6

Open Process

Figure 4:
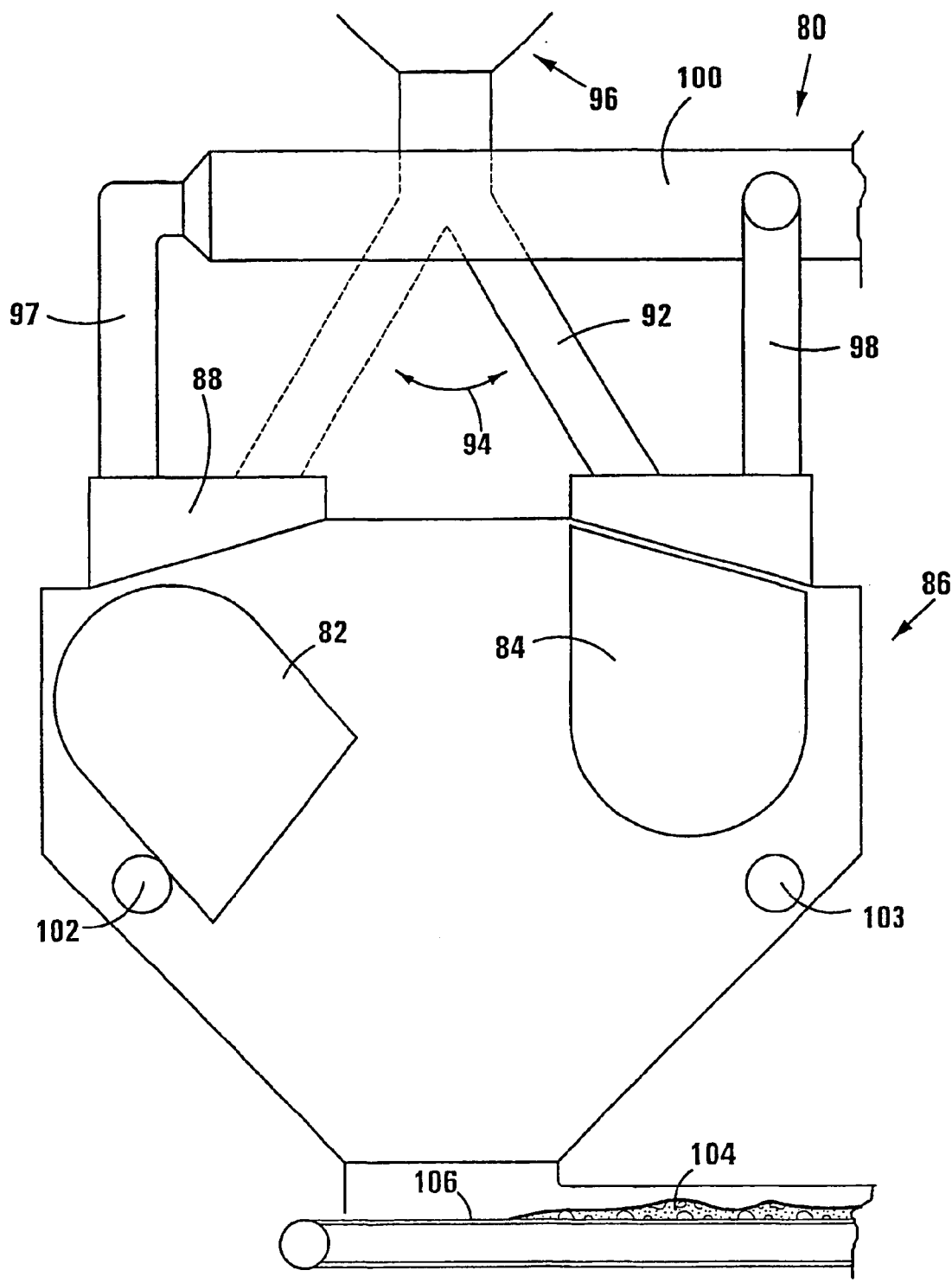
FIG. 4 shows a schematic side view of another installation for use in the method of the invention.

Referring now to FIG. 4, reference numeral 80 generally indicates another embodiment of an installation for the production of calcium 2-hydroxy-4-(mercaptomethyl) butanoic. The installation 80 includes a pair of reaction vessels or bins 82, 84 which are pivotally mounted within a housing, generally indicated by reference numeral 86. A part of the housing 86 forms a roof 88 above the bin 82 and a roof 90 above the bin 84. A feed conduit 92 extends from a reaction vessel 96. The conduit 92 can swivel in the direction of the arrow 94 so that it can feed reaction mixture from the reaction vessel 96 through the roofs 88, 90 into the bins 82, 84. Extraction conduits 97, 98 extend from the roofs 88, 90 to a common extraction conduit 100.

The bins 82, 84 are pivotally mounted so that they can be tipped (the bin 82 being depicted in its tipped position). Stop formations 102, 103 are provided below the bins 82, 84 and are positioned so that impact of the bin 82, 84 on the stop formation 102, 104 will serve to dislodge material in the bin 82, 84. Material 104 tipped from the bins 82, 84 falls onto a conveyor 106. In another embodiment of the invention (not shown), the stop formations 102, 104 are replaced with cam mechanisms which jolt the bins to dislodge the contents so that an entire load (up to 2 tons of material) is not dislodged in a single mass.

In the embodiment depicted in the drawings the bins are lined with polytetrafluoroethylene or a material having similar properties and have a capacity of about 3 m². The bins 82, 84 are approximately 1.9 m in diameter with a cylindrical section of about 0.5 m and a 1.9 m diameter hemispherical bottom. In the filling position as shown for bin 84, the bin 84 is substantially flush against the roof 90 above it. In another embodiment of the invention (not shown) the reactants are fed into the bin and fumes are removed from the bin via a common conduit. The installation 80 also includes mechanisms (not shown) for tipping the bins 82, 84 and for returning them to their untipped positions. The installation

80 also includes valves (not shown) in the extraction conduits 96, 98 which are closed by the PLC when the dropping mechanism is activated to prevent air being pulled through the relevant side of the extraction system. Each valve is reopened when the mechanism returns the bin to its upright position. In this embodiment of the invention, the PLC ensures that one bin is always in the filling position thus minimizing risk of damage to the extraction fan. The surge bin itself is partially closed off for example with small suctions in the roof (not shown) or via the enclosed belt conveyor.

The bins 82, 84 are fed via a revolving chute (not shown) under the exit of the reactor vessel 96. The chute swivels to feed bin 82 or 84 as required. This embodiment of the invention does not require a valve at the bin as the reactant flow is controlled from the reactor and material only flows down the chute when the bin is in its upright position. The inlet not in use permits air to be sucked through from the outside thereby minimizing odours in the general area.

This particular embodiment of the invention is relatively inexpensive. There are few moving parts, no operator exposure and the entire installation is enclosed.

Discussion

Calcium-2-hydroxy-4-(mercaptomethyl)butanoate is the α-hydroxy analogue of the calcium salt of methionine and is an important feed supplement, particularly for poultry. It is accordingly an important product in the animal feed industry.

The invention is based on the reaction between the acidic 2-hydroxy-4-(mercaptomethyl)butanoic acid and the basic calcium oxide. Calcium hydroxide may also be used but the reaction produces more moisture. The acid is in the form of an aqueous solution and the total moisture which has to be removed is the moisture arising from the solution and that produced in the reaction. The moisture content of the final product is preferably less than about 2% (m/m). The calcium oxide used in the process is not necessarily chemically pure and may contain limited quantities of calcium hydroxide and calcium carbonate. The amount of these impurities present influences the amount of heat generated. In addition, impurities in the calcium oxide such as magnesium oxide, iron and aluminium salts, sulphates and silica compounds can also influence the reaction. The physical nature and the way in which the calcium oxide is processed can also affect the reaction. It is accordingly difficult to predict whether or not a particular sample of calcium oxide will react satisfactorily to produce the desired free-flowing product. In those cases where the exothermicity of the reaction is insufficient to remove the required amount of water, a drying step can be introduced prior to storage or bagging.

There are effectively three ways in which the reaction can be carried out. These are referred to below as the "open process", the "totally enclosed batch process" and the "enclosed continuous process". All three processes are based on controlling the amount of acid in the form of a warm or hot aqueous solution of 2-hydroxy-4-(mercaptomethyl) butanoic acid and base in the form of calcium oxide or hydroxide used.

The Open Process

The open process is a continual batching operation. In this process, the combination of the raw materials and the frequency of batches is fast enough to match that of a continuous process even though each raw material batch is weighed individually. It is generally necessary to maintain the acid solution at a temperature of about 80–85° C. and, to achieve this, a separate heating tank is usually operated separately from the acid storage tank. As hot acid solution is drawn from the heating tank for use in the process, it is replenished by fresh acid solution via a heat exchanger. Alternatively, the heating tank can be fitted with internal or external heating coils.

The success of the process is determined by rapid and continuous batching of the raw materials, rapid mixing of the raw materials and rapid transfer of the reacting reaction mixture, or magma.

Material Dosing

In the dosing stage each of the raw materials i.e. water, the calcium oxide and the hot aqueous solution of the acid are measured separately but simultaneously and precise quantities are discharged sequentially into the mixing vessel. The operation is controlled by a programmable logic controller (or PLC) to ensure repeatability and accuracy of both the quantities and time intervals involved.

As soon as the acid or water tanks or the unslaked lime hopper which form parts of the mixing installation have been emptied, the PLC initiates the weighing sequence and refills the vessels with the correct quantities of material from storage. Thus, by the time the reaction mixture is ready for discharge from the reactor, the raw materials for the next batch have already been weighed out. Typically the discharging of the raw material takes about 3–10 seconds. However this may be significantly longer in the event of large quantities of lime with poor flow characteristics.

Mixing

The raw materials are discharged in sequence into the reactor with the acid discharged first followed by any formulation water. As soon as the valve opens to discharge the acid, the agitator starts. Once the acid valve has opened and the agitator has started, the PLC will dispense the water and open the lime discharge valve. After a preset interval, compressed air is blown into the lime weighing vessel to force the unslaked lime out. Thus the acid, water and lime are discharged almost simultaneously into the mixing zone created by the rotating agitator.

Mixing is continued for a predetermined time, usually between about 5 and 30 seconds. This time is determined by how rapidly the reaction mixture begins to boil. The mixing time can be longer in the case of a coarse or lower reactivity lime or where the acid is at a lower temperature than normal.

The mixer is linked to a fume extraction system to remove steam and fumes produced during the reaction.

The Rapid Transfer Stage

Initially, a liquid mixture comprising free acid, unslaked lime, water and some calcium-2-hydroxy-4-(mercaptomethyl)butanoate is present in the reactor. If this mixture is left in the reactor, the temperature rises rapidly, and the reaction mixture or magma starts to lose water and becomes extremely plastic and sticky. Ultimately this material would adhere to the mixing blades and the sidewall and transferring the material would be very difficult.

Before this happens, and after a preset time, the PLC opens the discharge valve of the reactor so that the reaction mixture is rapidly transferred into an adjacent unstirred reaction zone or den. The object of the rapid mixing step and rapid transfer is to initiate but not to complete the reaction between the acid and the unslaked lime so that the reaction is completed in a separate reaction zone.

After a preset time, the discharge valve on the reactor closes, and the entire cycle begins again. However, during the mixing and transfer periods, the acid, water and lime weighing vessels have been refilled with the desired quantity of raw materials. There is accordingly no significant time delay waiting for the weighing stages to be completed. The reacting magma usually takes approximately 3–15 seconds to discharge.

Final Reaction Stage

In the reaction zone, the reaction is allowed to go to completion. However in order to fully utilize the heat of reaction between the acid and the lime, several batches are dropped sequentially into the same reaction zone or den. Most of the steam and fumes arising from the reaction, occurs in this zone and accordingly every reaction zone and den is fitted with suitable fume and steam extraction equipment.

Once a den, or reaction zone, is full the reactor outlet swivels and commences discharging into a second (or third) adjacent den. The same sequence is followed until the second den is full. Whilst one den is filling up, the other(s) are matured or emptied. Generally the material remains in the static den for a period ranging from 15 to 60 minutes.

The material removed from the den is generally transported to a bay to mature and cool, or taken to further processing stages such as granulation, enrichment, cooling and dressing prior to packaging.

Typically one full batch cycle, which produces approximately 250 kg of the calcium salt product takes about 25–45 seconds.

Drying

It has been found that the initial product discharged from the dens has a moisture-content of about 3–5% and already contains at least 83% of the monomer acid. If this product is left to mature and cool in a bay, the mixture content drops to below 2% over a period of about a week. With the moisture loss, the monomer acid content rises typically to over 85%.

It is not desirable to leave the product in a heap for an extended period of time. Therefore the material is generally run through a drying stage. This results in the moisture content dropping to less than 2.0%, and as low as 0.5%, with a corresponding increase in monomer acid-content to above 85%. This is equivalent to over 96% expressed as the calcium salt.

The Totally Enclosed Batch Process

There are several differences between the "open process" and the "totally enclosed batch process".

In the "open process" the reacting magma is discharged into one or more static or moveable reaction zones or dens. These dens are fitted with fume extraction apparatus to remove the fumes and steam from the reaction area.

In the "totally enclosed batch process", there are a number of reaction dens on a carousel as described in Example 5 above. However all the dens are located within a single totally enclosed fume and steam extraction system. The raw material weighing system and reactor are usually separated from and positioned above position number 1 of the carousel. However fumes and steam arising in the weighers or in the reactor are also withdrawn to the fume extraction system.

Material is weighed out and discharged in a manner similar to the batch system. The charging time of the den is very similar to that of the "open process". Once a den has reached the desired level the carousel is rotated to position another den under the reactor discharge. The process is then repeated. Once the second den is filled, the carousel rotates again to position a fresh den under the reactor discharge.

The filled dens rotate on the carousel, with the reaction continuing within each den. Effectively the static dens of the "open process" are replaced with rotating bins.

The number of dens on the carousel is selected so that the reaction has time to proceed to completion before the den needs to be emptied and refilled. The larger the number of dens, the longer the period prior to refilling, and the greater the flexibility in modifying the plant throughput. The material remains in the rotating dens for a period of approximately 10–120 minutes, but usually around 20–30 minutes.

At the end of the cycle, the full den reaches the last position on the carousel before refilling. At this point a hydraulic arm tips the den, discharging the contents into a lined bin. The lined bin optionally contains a rotary cutter to break up any lumps formed.

However the tipping operation and top of the bin remain enclosed within the fume control system. The bin discharges the contents onto an enclosed handling system, such as a shrouded belt conveyor. This handling system takes the product to a maturation heap or for further processing.

Each den and the discharge bin are made from steel or a suitable composite material. There are no sharp corners within the dens or bin, and each vessel is lined with a suitable, slippery, temperature-resistant material, such as PTFE or similar. The lining is selected to withstand the maximum temperature reached during the reaction, but still release the product easily on tipping.

The den size is designed typically to take 500–1000 kg of the product and there are typically about 12–16 bins on the carousel.

In an embodiment of the invention, the reactor is fed by appropriate continuous handling/weighing systems. The material is accumulated in the reactor and discharged before the product thickens significantly. In another embodiment a continuous high-speed mixer with a short retention time is employed. A flap eliminates spillage during the rotation of the dens.

Enclosed Continuous Process

In the "enclosed continuous process" the same principles are followed as in both the open and the totally enclosed batch processes. As before, the key principles are: rapid weighing of the raw materials, rapid mixing, and rapid transfer to a reaction zone.

In different embodiments of the enclosed continuous process, the raw materials are weighed out either on a batch basis, as described for the totally enclosed batch process above, or on a continuous basis using continuous mass measuring apparatus and a high-speed continuous mixer with a short residence time.

Effectively a moving den in the form of an enclosed endless belt replaces the static or moving dens of the batch processes. The enclosed belt is fitted with extraction ports to extract steam and fumes to a fume handling system.

The enclosed continuous process is initiated by weighing the raw materials and discharging the weighed materials sequentially into the reactor as described in the previous examples. The charging time of the reactor is essentially the same as that of the batch processes described above. Again, in different embodiments, the reactor is discharged batchwise or continuously. The mixing time in the reactor is also essentially the same as that of the batch processes described above.

The reacting magma flows down a chute onto a suitable temperature-resistant endless flexible belt which is typically of a material such as thin stainless steel or PTFE. The belt speed can be varied to control the depth of material on the belt. In different embodiments, the belt is troughed (forming sidewalls and individual compartments) or folded on itself in the shape of a shallow "U". The belt slopes slightly away from the feed end towards the product discharge end so that reaction mixture or magma flows away from the feed end as long as it is still fluid.

The walls of the belt (or pockets of the troughed conveyor) form the bottom and sidewalls of the moving belt, eliminating spillage. A roof with at least one steam/fume extraction point runs the entire length of the conveyor so that steam and fumes produced during the reaction are removed to the fume handling system.

The reaction between the acid and unslaked lime proceeds essentially to completion on the belt. At a distance down the belt (determined by the plant capacity and speed of the belt) the material thickens, and acts as a dam wall against the further flow of fluid reacting magma.

At a point past the area where the material has hardened (nearer to the product discharge end), the belt flattens out. This is achieved by the belt running over a flat sloping plate or wide conveyor idler.

The flattening out of the product on the belt causes the heap of material travelling on the belt to pull apart, so that cracks and fissures are formed. The cracking up and crumbling of the surface allows steam and trapped fumes to escape. As this is taking place within the fume extraction hood, no fumes escape to the surrounding working area. The flattening out of the belt also results in the belt floor widening. This causes material to be dislodged from the sidewalls as they flatten out and reduces the chance of material adhering to the fume hood. At the end of the belt, the material falls into a lined bin equipped with a rotary cutter and rotating brushes clean the belt as it returns to the feed end. The material freed by the brushes drops into the bin. The top of the bin is enclosed within the fume extraction hood.

The bin discharges onto a suitable enclosed transport system, which moves the product to a maturation heap or for further processing.

Typically the product depth or thickness on the belt will be around 10–90 cm across a belt approximately 2 m wide. The enclosed system is typically up to 25 m long with a roof height of up to 2 m. The material remains on the belt for a period of from 10 to 120 minutes, depending on several factors (such as plant throughput and lime reactivity). The product can reach temperatures in excess of 230° C. whilst moving through the den.

Prior art methods for the production of the calcium salt of 2-hydroxy-4-(mercaptomethyl)butanoic acid of which the Applicant is aware include reacting the hydrolysis product of the corresponding nitrile with an aqueous lime slurry and reacting a basic calcium salt with 2-hydroxy-4-(mercaptomethyl)butanoic acid in the presence of a "heel" of the dry product calcium salt. The heel is usually a low grade form of the calcium salt containing between about 3 and 12% moisture. In the absence of a "heel", it has been reported that the reaction mass becomes viscous and difficult to mix. In these prior art processes, the "heel" is generally provided by recycling a portion of the product calcium salt back into the reaction mixture. For example, a prior art process known to the Applicant recycles 200 parts per hour out of 593 parts fed into a reaction zone. In the continuous process of this invention, no recycling is required. The process of the invention results in substantial cost savings since the additional equipment associated with transferring, measuring and controlling the recycle stream is not required. Effectively, the difference is between a recycle process and a Continuous Stirred Tank Reactor (CSTR) process. In an embodiment of the continuous process of the invention, an initial bed of the calcium salt product serves to replace the "heel" of the prior art. In another embodiment, most of the reaction occurs away from the mixing zone and no "heel" or bed of calcium salt is required. Similarly, the batch process of the invention requires no "heel". It is an advantage of the invention illustrated that the method of the invention, which involves a rapid mixing step followed by a rapid transfer step, produces a dry product containing less than 5% water, without the need to include a "heel" in the reaction mixture and without the viscosity problem reported in the prior art. An important feature of the invention is the rapid mixing of the calcium salt and the acid which allows the mixture to be transferred to the receiving vessel before it becomes too viscous. This, in turn, allows the heat build-up in the reaction mixture to drive off moisture to produce a free-flowing product with a low water content, typically less than 5%, without the need for a further expensive drying step. If a lower water content is required, the product can optionally be dried further.

The Applicant believes that the method of the invention will result in the cheaper and more efficient production of the calcium salt of 2-hydroxy-4-(mercaptomethyl)butanoic acid than that described in the prior art.

What is claimed is:

1. A method of making calcium-2-hydroxy-4-(mercaptomethyl)butanoate, the method including the steps of combining and mixing 2-hydroxy-4-(mercaptomethyl) butanoic acid and a calcium salt selected from calcium oxide and calcium hydroxide and water in a first reaction zone, the combining and mixing step being carried out over a first period of 3–120 seconds to produce a reaction mixture in the first reaction zone;

transferring the resulting reaction mixture at the end of the first period from the first reaction zone to a second reaction zone, the transferring step being carried out over a second period of 3–60 seconds; and allowing heat generated by reaction between the 2-hydroxy-4-(mercaptomethyl)butanoic acid and the calcium salt in the second reaction zone to drive off sufficient water to produce a product mixture containing less than 5% (m/m) water.

2. A method as claimed in claim 1, in which the first period is 5–20 seconds.

3. A method as claimed in claim 2, in which the second period is 5–40 seconds.

4. A method as claimed in claim 1, in which the 2-hydroxy-4-(mercaptomethyl)butanoic acid is in the form of an aqueous solution.

5. A method as claimed in claim 4, in which the aqueous solution has a concentration of 65–95% by mass of the 2-hydroxy-4-(mercaptomethyl)butanoic acid.

6. A method as claimed in claim 5, in which the aqueous solution has a concentration of 70–90% by mass.

7. A method as claimed in claim 4, in which the combining and mixing steps are conducted so that the reaction mixture contains 70–90% by mass of the aqueous solution, 10–30% by mass of the calcium salt and 0–20% by mass of water.

8. A method as claimed in claim 1, in which the heat generated is allowed to drive off sufficient water to produce a product mixture containing less than 4.5% water.

9. A method as claimed in claim 1, in which the heat generated is allowed to drive off sufficient water to produce a product mixture containing less than 2% water.

10. A method as claimed in claim 4, which includes the prior step of warming the solution of 2-hydroxy-4-(mercaptomethyl)butanoic acid to 50–130° C.

11. A method as claimed in claim 4, which includes the prior step of warming the solution of 2-hydroxy-4-(mercaptomethyl)butanoic acid to 70–85° C.

12. A method as claimed in claim 4, in which the calcium salt is calcium oxide and in which 55–65 kg of the aqueous solution is combined with 9–18 kg of the calcium salt over a first period of 3–10 seconds.

13. A method as claimed in claim 12, in which the duration of the second period is 3–15 seconds.

14. A method as claimed in claim 4, in which 450–550 kg of the aqueous solution is combined with 75–150 kg of the calcium salt over a first period of 3–30 seconds.

15. A method as claimed in claim 14, in which the duration of the second period is 3–20 seconds.

16. A method as claimed in claim 1, which includes the further steps of successively combining and mixing a plurality of batches of the acid, calcium salt and water in the first reaction zone to produce successive batches of the reaction mixture and successively transferring each of the batches to the same second reaction zone.

17. A method as claimed in claim 16, in which a material dosing system, controlled by a programmable logic controller, weighs out the raw materials into the first reaction zone.

18. A method of making calcium-2-hydroxy-4-(mercaptomethyl)butanoate, the method including the steps of combining and mixing 2-hydroxy-4-(mercaptomethyl)butanoic acid, a calcium salt selected from calcium oxide and calcium hydroxide and water in a first reaction zone to produce a reaction mixture in the first reaction zone; and continuously transferring the reaction mixture from the first reaction zone to a second reaction zone, the reactants being added to the first reaction zone in successive batches and the reaction mixture being continuously removed from the first reaction zone at a rate which is selected so that the residence time of the reaction mixture in the first reaction zone is 5–60 seconds; and allowing heat generated by reaction between the 2-hydroxy-4-(mercaptomethyl)butanoic acid and the calcium salt in the second reaction zone to drive off sufficient water to produce a product mixture containing less than 10% water.

19. A method as claimed in claim 18, in which the heat is allowed to drive off sufficient water to produce a product mixture containing less than 5% water.

20. A method as claimed in claim 18, in which the rate of removal of the reaction mixture from the first reaction zone is 500–30000 kg per hour.

21. A continuous method of making calcium-2-hydroxy-4-(mercaptomethyl)butanoate, the method including the steps of simultaneously feeding, into a reaction zone, an aqueous solution of 2-hydroxy-4-(mercaptomethyl)butanoic acid, at a rate of approximately 500–30000 parts per hour, and a calcium salt selected from calcium oxide and calcium hydroxide, at a rate of approximately 150–6200 parts per hour, to produce a reaction mixture in the reaction zone; and transferring the reaction mixture from the reaction zone to a second zone at a rate which is selected so that the residence time of the reaction mixture in the reaction zone is 5–60 second and is sufficient to initiate reaction between the 2-hydroxy-4-(mercaptomethyl)butanoic acid and the calcium salt but not sufficient to drive off water from the reaction mixture and allowing heat generated by further reaction between the 2-hydroxy-4-(mercaptomethyl)butanoic acid and the calcium salt in the second zone to drive off sufficient water to produce a product mixture containing less than 5% water.

22. A method as claimed in claim 21 in which the second zone is an endless moving belt.

23. The calcium salt of 2-hydroxy-4-(mercaptomethyl)butanoate prepared by a method as claimed in claim 1.

24. A method of making a salt of 2-hydroxy-4-(mercaptomethyl)butanoate, the salt being a salt of a metal selected from magnesium, sodium and potassium and the method including the steps of combining and mixing 2-hydroxy-4-(mercaptomethyl)butanoic acid and a base selected from magnesium oxide, sodium hydroxide and potassium hydroxide in water in a first reaction zone, the combining and mixing step being carried out over a first period of 3–120 seconds to produce a reaction mixture in the first reaction zone;

transferring the resulting reaction mixture at the end of the first period from the first reaction zone to a second reaction zone, the transferring step being carried out over a second period of 3–60 seconds; and allowing heat generated by reaction between the 2-hydroxy-4-(mercaptomethyl)butanoic acid and the base in the second reaction zone to drive off sufficient water to produce a product mixture containing less than 5% (m/m) water.

25. A magnesium, sodium or potassium salt of 2-hydroxy-4-(mercaptomethyl)butanoic acid prepared by a method as claimed in claim 24.

* * * * *